United States Patent [19]

Blumenfeld et al.

[11] 4,166,075

[45] Aug. 28, 1979

[54] METHOD OF PREPARING XYLENES CHLORINATED IN THE NUCLEUS

[75] Inventors: Georg Blumenfeld, St. Augustin; Paul Riegger, Troisdorf, both of Fed. Rep. of Germany

[73] Assignee: Dynamit Nobel Aktiengesellschaft, Troisdorf, Fed. Rep. of Germany

[21] Appl. No.: 870,400

[22] Filed: Jan. 18, 1978

[30] Foreign Application Priority Data

Jan. 25, 1977 [DE] Fed. Rep. of Germany ....... 2702829

[51] Int. Cl.$^2$ ............................................. C07C 25/04
[52] U.S. Cl. ................................................. 260/650 R
[58] Field of Search ..................................... 260/650 R

[56] References Cited

U.S. PATENT DOCUMENTS 3,509,204  4/1970  Selwitz ............................. 260/650 R

OTHER PUBLICATIONS

Weigandt et al., I & E C, vol. 43, Sep. 1951, pp. 2167–2172.

Primary Examiner—C. Davis
Attorney, Agent, or Firm—Sprung, Felfe, Horn, Lynch & Kramer

[57] ABSTRACT

An improvement in a process for preparing a xylene chlorinated in the nucleus by contacting the xylene with chlorine in the presence of a catalyst, the improvement residing in employing as the catalyst an iron halide or antimony halide and employing a co-catalyst which is an aliphatic, halogenated or nonhalogenated hydrocarbon having an oxygen function.

17 Claims, 1 Drawing Figure

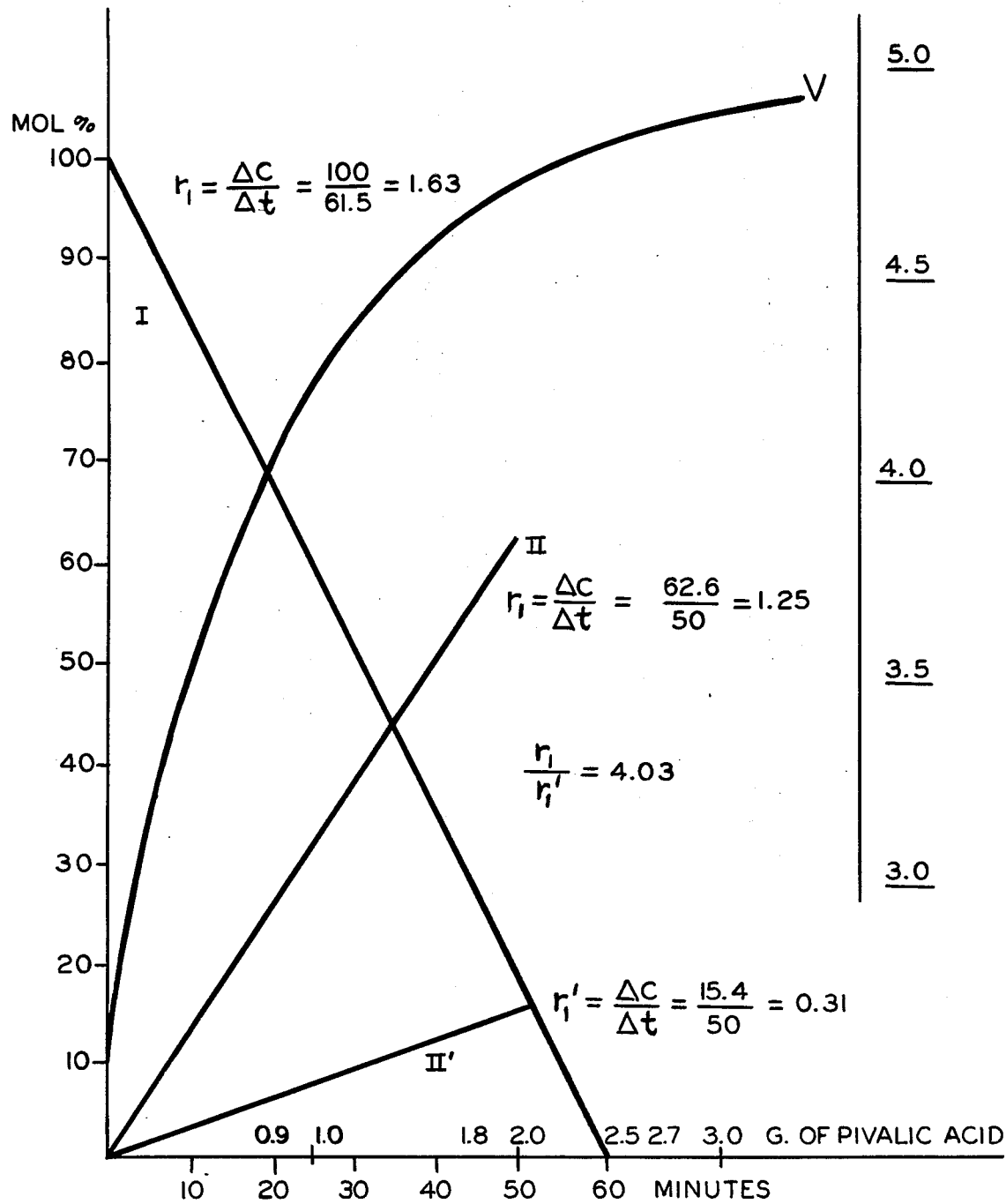

METHOD OF PREPARING XYLENES CHLORINATED IN THE NUCLEUS

BACKGROUND

1. Field of the Invention

The subject of the invention is a method of preparing xylenes chlorinated in the nucleus, especially 2,5-dichloro-p-xylene, by the reaction of xylenes, especially p-xylene, with chlorine in the presence of a catalyst system.

2. Discussion of the Prior Art

The chlorination of xylenes in the nucleus in the presence of Friedel-Crafts catalysts, generally $FeCl_3$, is known. For example, in U.S. Pat. No. 2,421,389, the chlorination of p-xylene in the presence of a Friedel-Crafts catalyst and $CCl_4$ is described, wherein monochloroxylene, 2,3- and 2,5-dichloro-p-xylene, and trichloro-p-xylene are formed together.

For the controlled preparation of a specific product, it is necessary to strive for selective chlorination.

Selective chlorination processes for the preparation of 2,5-dichloro-p-xylene are described in U.S. Pat. No. 3,002,027, German Offenlegungsschrift No. 2,604,277 and German Offenlegungsschrift No. 2,604,278.

In U.S. Pat. No. 3,002,027, glacial acetic acid is used as solvent. This, however, entails disadvantages in the working up of the reaction mixture and in the recovery of the solvent.

In German Offenlegungsschrift No. 2,604,277 organic sulfur compounds are used as co-catalysts in conjunction with $FeCl_3$ and $SbCl_3$, which due to their extremely offensive odor involve difficulties in handling and in the working up of the reaction mixture. The antimony and iron sulfides used as catalysts in German Offenlegungsschrift No. 2,604,278 furthermore require very long chlorination times.

THE INVENTION

The present invention is addressed to the object of creating a process which will permit the selective nuclear chlorination of xylenes while avoiding the disadvantages of the methods known hitherto.

One special object of the invention consists preparing 2,5-dichloro-p-xylene in a high yield by the chlorination of p-xylene.

The foregoing objects are accomplished in accordance this invention which comprises a process for preparing a nuclear chlorinated xylene which process comprises contacting a xylene with chlorine in the presence of an iron halide or antimony halide catalyst and an aliphatic, halogenated or unhalogenated hydrocarbon co-catalyst having an oxygen function.

In the process of the invention, unusual changes in the proportions of the isomers take place in the production of the dichlorination products vis-a-vis the known processes. For example, in the dichlorination of p-xylene in particular, a mixture of 2,5- and 2,3-dichloro products is formed containing a comparatively small percentage of trichloro product, the isomer composition being shifted in favor of the 2,5 product. In the chlorination of o- or m-xylene, shifts in the isomer composition of the dichloro products are less pronounced, but the formation of the trichloro product is likewise definitely suppressed.

The chlorination of the xylenes can be performed in the presence of a solvent such as chloroform, carbon tetrachloride, perchloralkanes and the like, that is, in solvents which are inert with respect to chlorine under the chlorination conditions. Carbon tetrachloride is used preferentially as the solvent.

The reaction is generally performed in the temperature range from 10° to 150° C., preferably at temperatures between 20° and 80° C. When operating without solvent, it is desirable to use temperatures at which the reaction mixture is fluid.

The amount of chlorine to be introduced per unit of time is desirably regulated such that a uniform absorption of chlorine takes place. For the achievement of a maximum yield, especially of the industrially important 2,5-dichloro-p-xylene, it is advantageous to use an approximately stoichiometric amount of chlorine, for example about 1.9 to 2.2 moles of chlorine per mole of p-xylene in the production of 2,5-dichloro-p-xylene.

The process of the invention can be performed at standard pressure, or also, if desired, at elevated pressure or less than atmospheric pressure, although standard pressure is preferred.

The working up of the reaction mixture can be performed simply by removing the catalysts and co-catalysts by washing the reaction mixture with water and separating the solvent, if used, and any residual amounts of co-catalyst, by distillation. The isolation of the reaction mixture products does not entil any environmental problems.

The preferred catalyst of the iron halide group is $FeCl_3$, and that of the antimony halide group is $SbCl_3$.

The iron halides or antimony halides serving as catalysts are used in amounts of 0.01 to 0.5 mole-%. with respect to the product being chlorinated.

The aliphatic, halogenated or unhalogenated hydrocarbons having an oxygen function, which are used as co-catalysts in accordance with the invention, are used generally in a one to twenty times molar amount with respect to the metal halides, preferably in a one to ten times molar amount, and especially in a two to five times molar amount. With respect to the product to be chlorinated, the co-catalysts are accordingly used in amounts of 0.01 to 10 mole-%, preferably 0.01 to 5 mole-%, and especially 0.02 to 2.5 mole-%.

Co-catalysts which are suitable in the meaning of the invention are those of the general formula R-X, wherein X=OH or —CO—R' or —COOH, R' being H or an alkyl group of 1 to 5 carbon atoms, and R being a linear or branched $C_1$ to $C_{17}$ hydrocarbon moiety, preferably an alkyl moiety. The hydrocarbon moiety can be halogenated if desired. The halogenated or unhalogenated hydrocarbon moiety can have one or more carboxyl groups (e.g., terminal and/or middle) if X is —COOH. Also, if X is —COOH, R can represent hydrogen.

Additionally the moiety R can be a saturated or unsaturated aliphatic moiety such as alkenyl, alkinyl and such groups can have up to 17 carbon atoms.

Suitable co-catalysts are preferably those which are derived from saturated (acyclic) hydrocarbons, such as for example alkanoic acids or polycarboxylic acids, e.g., alkane diacids or primary or secondary or tertiary alkanols or corresponding aldehydes or ketones.

The following are mentioned by way of example: methanol, ethanol, n-propanol, isopropanol, isobutanol, tert.-butanol, trichloro-tert.-butanol, formic acid, acetic acid, propionic acid, isobutyric acid, pivalic acid, stearic acid, malonic acid, isobutyraldehyde, acetone.

Co-catalysts of especially good activity and selectivity which are preferred in accordance with the invention, especially in the preparation of 2,5-dichloro-p-xylene, are those of the general formula R-X wherein X has the meaning given above and R is a linear or branched, halogenated or unhalogenated alkyl moiety of 2 to 5 carbon atoms.

Especially preferred co-catalysts are isobutanol, isobutyraldehyde or pivalic acid. Pivalic acid is especially suitable as a co-catalyst in the production of the particularly important 2,5-dichloro-p-xylene.

An especially preferred catalyst system contains antimony trichloride or antimony pentachloride as catalyst and pivalic acid as co-catalyst.

It is to be assumed that the aliphatic hydroxyl, carbonyl and carboxyl compounds serving as co-catalysts will form a metal halide complex compound, e.g., an $FeCl_3$ complex compound, in the relatively unpolar reaction medium. It is surprising that these complex compounds are active, because it is known, for example, from Friedel-Crafts acylation, that stoichiometric amounts of $FeCl_3$ or $AlCl_3$ are needed because the carbonyl compound that forms binds and thus deactivates the catalyst-complex combination.

Whereas hydroxyl and carbonyl compounds, when used as co-catalysts, have a somewhat retardant effect on the rate of transformation to the dichloro product, this is not so much the case with the carboxyl compounds. With regard to further chlorination to the trichloro compound, however, a great retardation takes place. The most effective compounds are, as described above, isobutanol, isobutyraldehyde and pivalic acid.

In a parallel reaction, the additives can likewise become chlorinated to a greater or lesser extent, without destroying the effect. Thus, isobutanol can become oxidized to isobutyraldehyde and chlorinated, while pivalic acid remains virtually unchanged. Pivalic acid also has no effect on the rate of transformation to the dichloro product. The use of pivalic acid and $FeCl_3$ complex compound as a chlorination catalyst system produces especially good results in the preparation of 2,5-dichloro-p-xylene, the yield increasing from 48 to 50% without co-catalyst (Example 1 with $FeCl_3$ alone) to about 78%, 80.5% and 81.11% (Examples 13, 29 and 30). In Example 1, when the 2,5 isomer production is at its maximum, the monochloro compound is still present in addition to the 2,3 isomer and the trichloro compound. In the chlorination of p-xylene in the presence of pivalic acid and $FeCl_3$ or $SbCl_3$ or $SbCl_5$, it is possible to conduct the reaction such that the monochloro compound disappears and thus the 2,5-dichloro compound can be obtained directly as a low-boiling isomer top product by rectification. Thus, 2,5-dichloro-p-xylene can be prepared in a simple manner, in a high yield, with a purity of 99.8%.

2,5-dichloro-p-xylene is a valuable foreproduct for the preparation of a special dye. By oxidation of the side chains or by their full chlorination followed by hydrolysis, 2,5-dichloroterephthalic acid or its dichloride can be produced, from which polyesters or polyamides, respectively, can be produced with specific properties.

The process of the invention also makes possible the selective chlorination of o- or m-xylene to the xylenes chlorinated in the nucleus, especially dichloroxylenes. As shown by Examples 15 and 16 and Examples 18 and 19, when the catalyst system of the invention is used, the dichloro compounds are formed in a high yield. The isomers can be separated from one another, for example by distillation or by crystallization.

The dichloro compounds of o- and m-xylene can likewise be used for the production of foreproducts for polymers.

In order to more fully illustrate the nature of the invention in a manner of practicing the same the following examples are presented:

EXAMPLES

The invention will be explained with the aid of the following examples. Examples 1, 14, 17 and 20 serve for purposes of comparison (without co-catalyst), and Example 27 as well.

The appended graph relating to Examples 24 and 26 serves to demonstrate the effectiveness of the catalyst system used in accordance with the invention:

Curve I = Concentration of monochloroxylene as a function of the chlorination time;

Curve II = Concentration of 2,5-dichloro-p-xylene as a function of the chlorination time;

Curve II' = Concentration of 2,3-dichloro-p-xylene as a function of the chlorination time.

In the case of curves I, II and II', the ordinates indicate the molar percentages and the abscissas the minutes.

Curve V shows the rationship between the amount of pivalic acid used and the ratio of the rates of formation of 2,5-dichloro-p-xylene and 2,3-dichloro-p-xylene (abscissas = g of pivalic acid put in, ordinates = $r_1/r'_1$).

Examples 1–13

A mixture of 106 g of xylene (1 mole), 190 ml of carbon tetrachloride and 0.6 g of $FeCl_3$ (0.57 wt.-%, 0.37 mole-% with respect to xylene) was chlorinated in a 500 ml glass flask shielded from light and equipped with a gas introduction tube, thermometer, stirrer and reflux condenser, and a gas discharge tube. By means of a bath, the temperature was held constant at 40° C., and the chlorine throughput amounted to 1 mole of chlorine per hour.

The chlorinations were performed with the addition of a variety of co-catalysts with p-, o- and m-xylene, while striving for a uniform absorption of chlorine which results in a maximum yield of dichloro compound. The analysis was performed by gas chromatography.

The following table shows the distribution of the products of the chlorination of p-xylene in the nucleus. Monochloroxylene (I), the two isomeric dichloroxylenes (II/2,5) and (II/2,3) and trichloroxylene (III). $U_k$ represents the transformation to products chlorinated in the nucleus. The difference from 100 consists substantially of higher boiling products which are formed by Friedel-Crafts alkylation from products chlorinated on the side chain. When pivalic acid is the co-catalyst, $U_k$ is especially high.

Table

| Ex. | Co-catalyst | I | II(2,5) | II(2,3) % | III | $U_k$ | Molar ratio of co-cat. to $FeCl_3$ |
|---|---|---|---|---|---|---|---|
| 1 | — | 4.8 | 49.9 | 20.4 | 22.9 | 98.0 | — |
| 2 | Methanol | — | 62.6 | 21.6 | 7.0 | 91.2 | 15 |
| 3 | Ethanol | — | 67.7 | 14.4 | 10.8 | 92.9 | 10.7 |
| 4 | n-Propanol | — | 74.0 | 8.1 | 7.6 | 89.7 | 7.6 |
| 5 | i-Propanol | — | 71.0 | 12.0 | 5.2 | 88.2 | 7.6 |
| 6 | i-Butanol | — | 71.7 | 9.2 | 8.8 | 89.7 | 5.8 |
| 7 | tert.-Butanol | — | 67.3 | 22.6 | 8.6 | 98.5 | 5.8 |

Table-continued

| Ex. | Co-catalyst | I | II(2,5) | II(2,3) % | III | $U_k$ | Molar ratio of co-cat. to $FeCl_3$ |
|---|---|---|---|---|---|---|---|
| 8 | Trichloro-tert.-butanol | — | 56.5 | 10.8 | 27.1 | 95.4 | 2.7 |
| 9 | Formic acid | 0.6 | 54.0 | 21.0 | 20.6 | 96.2 | 9.4 |
| 10 | Acetic acid | 0.1 | 62.4 | 22.4 | 3.45 | 88.35 | 7.2 |
| 11 | Propionic acid | — | 59.3 | 20.1 | 7.6 | 92.8 | 5.8 |
| 12 | Isobutyric acid | — | 66.5 | 22.0 | 4.2 | 92.7 | 4.9 |
| 13 | Pivalic acid | — | 78.0 | 13.8 | 7.3 | 99.1 | 5.6 |

Examples 14–16

In the experimental apparatus described above, o-xylene was chlorinated instead of p-xylene. In the chlorination of o-xylene in the nucleus, two monochloro compounds are formed:

3- and 4-chloro-o-xylene (I), three dichloro compounds: (II)/

3,4; II/4,5 and II/3,6, and two trichloro compounds (III).

Table

| Ex. | Co-catalyst | I | II/3,4 +II/3,6 | II/4,5 % | III | $U_k$ | Molar ratio of co-cat. to $FeCl_3$ |
|---|---|---|---|---|---|---|---|
| 14 | — | 1.21 | 37.1 | 23.4 | 35.8 | 97.5 | — |
| 15 | Ethanol | — | 36.3 | 51.3 | 11.2 | 98.8 | 10.7 |
| 16 | Pivalic acid | 3.35 | 44.4 | 42.6 | 8.3 | 95.3 | 4.25 |

Examples 17–19

In the apparatus described, m-xylene is chlorinated instead of p-xylene.

In the chlorination of m-xylene in the nucleus, two monochloro compounds (I), two dichloro compounds (II) and three trichloro compounds (III) are mainly formed.

Table

| Example | Co-catalyst | I | II | III % | $U_k$ | Molar ratio of co-cat. to $FeCl_3$ |
|---|---|---|---|---|---|---|
| 17 | — | — | 68.0 | 30.0 | 98.0 | — |
| 18 | Ethanol | — | 91.2 | 3.2 | 94.4 | 10 |
| 19 | t-Butanol | 6.8 | 86.0 | 4.1 | 96.9 | 5.8 |

Examples 20–26

The differences in isomer formation during the chlorination is based on the changes produced in the rates of reaction by the catalyst complex. Consequently, monochloro-p-xylene(I) and an equimolecular mixture of 2,3-dichloro-p-xylene and 2,5-dichloro-p-xylene(II) were chlorinated in the experimental apparatus of Example 1, under the same conditions, at 25° C., and the course of the chlorination was analyzed by gas chromatography based on continuous sampling. The concentration-time functions of the disappearing and forming products are linear, and give constant rates of transformation which are numerically expressable and comparable. Mathematical expressions of the effectiveness are obtained from the ratio of the rates of formation of the isomers.

$r_{1br}$: gross rate of the chlorination of I to II/2,5 $(r_1)+II/2,3 \ (r'_1)$ $r_{2br}$: gross rate of chlorination to the trichloro compound (III) from II/2,5 $(r_2)+II/2,3 \ (r'_2)$.

Table

| Ex. No. | Co-cat. | I $r_{1br}$ | $r_1/r'_1$ | Ex. No. | II/2,5 + II/2,3 $r_{2br}$ | $r_2/r'_2$ | $r_{1br}/r_{2br}$ |
|---|---|---|---|---|---|---|---|
| | | Mole-% per minute | | | | | |
| 20 | — | 1.58 | 2.45 | 20a | 1.20 | 1.88 | 1.3 |
| 21 | Isobutanol | 0.82 | 4.15 | 21a | 0.07 | 4.4 | 11.7 |
| 22 | Isobutyraldehyde | 1.22 | 4.22 | | | | |
| 23 | Acetone | 1.26 | 2.7 | | | | |
| 24 | Pivalic acid (0.9 g) | 1.63 | 4.03 | | | | |
| 25 | Pivalic acid (1.8 g) | 1.57 | 4.67 | 25a | 0.2 | 5.3 | 7.85 |
| 26 | Pivalic acid (2.7 g) | 1.54 | 4.88 | | | | |
| 27 | Glacial acetic acid | 0.7 | 4.37 | | | | |

Example 27

Chlorination of I in glacial acetic acid at 70° C. in accordance with Example 1 of U.S. Pat. No. 3,002,027 with four times the amount of glacial acetic acid with respect to I.

Example 28

1,700 g of p-xylene (16 moles), 3 liters of carbon tetrachloride, 9.3 g of $FeCl_3$ (0.057 mole) and 27 g of pivalic acid (0.264 mole) are chlorinated in the six-liter flask at 20°–40° C. with external cooling, by introducing approximately 5.5 moles of $Cl_2/h$ through a feed tube, with stirring, for 6.3 hours. The chlorine transformation is 100% in the first 4 hours, and then falls off, for a total of 97%.

| $U_k$ Raw prod. | I | II/2,5 | II/2,3 % | III |
|---|---|---|---|---|
| 99.48 | | 78.66 | 15.11 | 5.61 |

The raw product is washed with water, dewatered azeotropically during the distilling of the carbon tetrachloride, and rectified in an active column at 33 Torr. II/2,5 was obtained with a purity of 99.8%. The distillation of the sump product, which was substantialy II/2,3 and III, yielded a residue of 50 g or 2%.

Example 29

In an experimental apparatus similar to that of Example 1, 250 g of p-xylene (2.36 moles) was chlorinated at 20°–26° C. for 2 h 20 min with the addition of 0.5 g of antimony trichloride (0.0022 mole) and 1 g of pivalic acid (0.01 mole). The chlorine transformation was 91%.

| I | II(2,5) | II(2,3) | III | Molar ratio co-cat.:SbCl₃ |
|---|---------|---------|-----|---------------------------|
| 0.36 | 80.5 | 15.62 | 2.69 | 4.56 |

Example 30

As in Example 29, 126 g of p-xylene (1.18 mole) was chlorinated at 20°–30° C. for 70 minutes with the addition of 2.3 g of SbCl₅ (0.0077 mole) and 2.0 g of pivalic acid (0.02 mole). The chlorine transformation was 90%.

| I | II(2,5) | II(2,3) | III | Molar ratio co-cat.:SbCl₅ |
|---|---------|---------|-----|---------------------------|
| 0.09 | 81.11 | 15.31 | 3.36 | 2.5 |

We claim:

1. In a process for preparing a xylene chlorinated in the nucleus by contacting xylene with chlorine in the presence of a catalyst, the improvement which comprises employing as the catalyst an iron halide or antimony halide and employing a co-catalyst which co-catalyst is an aliphatic, halogenated or unhalogenated hydrocarbon having an oxygen function.

2. A process according to claim 1 wherein the catalyst is in the amount of 0.01 to 0.05 mole-% and the co-catalyst is present in the amount of 0.01 to 10 mole-%, both based upon the amount of xylene to be chlorinated.

3. A process according to claim 2 wherein the co-catalyst is present in the amount of 0.02 to 5 mole-%, based upon the amount of xylene to be chlorinated.

4. A process according to claim 1 wherein said co-catalyst has the formula RX wherein X is hydroxyl, —CO—R' or —COOH, R' represents hydrogen or alkyl group of 1 to 5 carbon atoms and R represents a linear or branched $C_1$ to $C_{17}$ hydrocarbon moiety which optionally can be halogenated and where X represents a —COOH group can contain one or more additional —COOH groups or when X is a COOH group R can be hydrogen.

5. A process according to claim 4 where R represents a linear or branched alkyl moiety having 2 to 5 carbon atoms.

6. A process according to claim 5 wherein the co-catalyst is isobutanol, isobutyraldehyde or pivalic acid or a mixture thereof.

7. A process according to claim 1 wherein the reaction is carried out at a temperature of 10° to 150° C.

8. A process according to claim 7 wherein the process is carried out at a temperature of 20° to 80° C.

9. A process according to claim 1 wherein the co-catalyst is an alkanoic acid, a polycarboxylic acid, a primary, secondary or tertiary alkanol or the corresponding halide or ketone of a primary, secondary or tertiary alkanol.

10. A process according to claim 1 wherein the co-catalyst is methanol, etnanol, n-propanol, isobutanol, tert.-butanol, trichloro-tert.-butanol, formic acid, acetic acid, propionic acid, isobutyric acid, pivalic acid, stearic acid, malonic acid, isobutyraldehyde or acetone.

11. A process according to claim 9 wherein the catalyst is antimony trichloride or antimony pentachloride.

12. A process according to claim 9 wherein the catalyst is iron trichloride.

13. A process according to claim 1 wherein p-xylene is chlorinated.

14. A process according to claim 1 wherein the catalyst is an antimony halide.

15. A process according to claim 1 wherein said co-catalyst has the formula RX wherein X is hydroxyl or —CO—R' wherein R' represents hydrogen or an alkyl group of 1 to 5 carbon atoms and R represents a linear or branched $C_1$ to $C_{17}$ hydrocarbon moiety which optionally can be halogenated.

16. A process according to claim 1 wherein the co-catalyst is a polycarboxylic acid, a primary, secondary or tertiary alkanol or the corresponding halide or ketone of the primary, secondary or tertiary alkanol.

17. A process according to claim 1 wherein the chlorine is $Cl_2$.

* * * * *